United States Patent [19]

Lawin et al.

[11] Patent Number: 5,792,478
[45] Date of Patent: Aug. 11, 1998

[54] TISSUE INJECTABLE COMPOSITION AND METHOD OF USE

[75] Inventors: Timothy P. Lawin, Vadnais Heights; Dean Klein, Lindstrom, both of Minn.

[73] Assignee: Advanced Uro Science, St. Paul, Minn.

[21] Appl. No.: 676,592

[22] Filed: Jul. 8, 1996

[51] Int. Cl.$^6$ .............. A61F 2/02; A61F 2/08; A61K 9/14; A61K 9/50
[52] U.S. Cl. .......... 424/502; 424/426; 424/489; 424/501; 523/113; 523/114; 623/14; 623/16
[58] Field of Search .................. 424/426, 489, 424/501, 502; 523/113, 114; 623/14, 16

[56] References Cited

U.S. PATENT DOCUMENTS

| | | | |
|---|---|---|---|
| 3,638,649 | 2/1972 | Ersek | 128/214 R |
| 3,657,744 | 4/1972 | Ersek | 3/1 |
| 3,783,868 | 1/1974 | Bokros | 128/260 |
| 3,977,896 | 8/1976 | Bokros et al. | 427/213 |
| 4,129,470 | 12/1978 | Homsy | 156/155 |
| 4,197,846 | 4/1980 | Bucalo | 128/218 P |
| 4,239,492 | 12/1980 | Holman et al. | 8/94.11 |
| 4,240,794 | 12/1980 | Holman et al. | 8/94.11 |
| 4,424,208 | 1/1984 | Wallace et al. | 424/177 |
| 4,469,676 | 9/1984 | Hecmati | 424/95 |
| 4,527,293 | 7/1985 | Eckstein et al. | 623/12 |
| 4,563,350 | 1/1986 | Nathan et al. | 424/95 |
| 4,703,108 | 10/1987 | Silver et al. | 530/356 |
| 4,773,393 | 9/1988 | Haber et al. | 600/30 |
| 4,776,890 | 10/1988 | Chu | 106/161 |
| 4,795,467 | 1/1989 | Piez et al. | 623/16 |
| 4,803,075 | 2/1989 | Wallace et al. | 424/423 |
| 4,863,732 | 9/1989 | Nathan et al. | 424/95 |
| 4,865,602 | 9/1989 | Smestad et al. | 623/16 |
| 4,902,511 | 2/1990 | Kronman | 424/423 |
| 4,992,226 | 2/1991 | Piez et al. | 264/109 |
| 5,001,169 | 3/1991 | Nathan et al. | 523/113 |
| 5,007,940 | 4/1991 | Berg | 623/66 |
| 5,011,494 | 4/1991 | von Recum et al. | 623/11 |
| 5,116,387 | 5/1992 | Berg | 623/66 |
| 5,158,573 | 10/1992 | Berg | 623/66 |
| 5,204,382 | 4/1993 | Wallace et al. | 523/115 |
| 5,256,418 | 10/1993 | Kemp et al. | 424/423 |
| 5,258,028 | 11/1993 | Ersek et al. | 623/11 |
| 5,306,500 | 4/1994 | Rhee et al. | 424/422 |
| 5,328,955 | 7/1994 | Rhee et al. | 525/54.1 |
| 5,336,263 | 8/1994 | Ersek et al. | 623/11 |
| 5,352,715 | 10/1994 | Wallace et al. | 523/115 |
| 5,376,375 | 12/1994 | Rhee et al. | 424/423 |
| 5,399,351 | 3/1995 | Leshchiner et al. | 424/422 |
| 5,407,445 | 4/1995 | Tautvydas et al. | 623/8 |
| 5,451,406 | 9/1995 | Lawin et al. | 424/423 |
| 5,480,644 | 1/1996 | Freed | 424/436 |

OTHER PUBLICATIONS

Henly et al., "Particulate Silicone for Use in Periurethral Injections: Local Tissue Effects and Search for Migration", American Crological Association, Inc. Copyright 1996, pp. 2039–2043.

Kawanabe et al., "Effects of Injecting Massive Amounts of Bioactive Ceramics in Mice", *Journal of Biomedical Materials Research*, vol. 25, 1991, pp. 117–128.

Hench, et al., "Bioglass Implants for Otology", *Biomaterials in Otology*, Martinus Nijhoff Publishers, 1984, pp. 62–69.

Borovetz, PhD. et al., "Protein Adsorption in vitro onto BNiomaterial Surfaces Covered with Ulti Carbon", *Med. Dev.*, 10(3), 187–203, (1982).

(List continued on next page.)

*Primary Examiner*—Carlos Azpuru
*Attorney, Agent, or Firm*—Nawrocki, Rooney & Sivertson, P.A.

[57] ABSTRACT

An improved biocompatible composition consisting of physiologically stable beads or particles carried in a lubricative suspension, solution, other fluid or gel. The composition is intended to be delivered into the body through a small-bored needle, cannula, or other catheter into a tissue site for the purpose of augmenting the tissue. In particular, the composition is useful for augmenting tissue in the area of the cardiac orifice of the stomach to reduce gastric reflux, in the area of the internal or external sphincter of the anal canal to reduce fecal incontinence or in the area of urethral tissue for the purpose of treating urinary incontinence.

19 Claims, 1 Drawing Sheet

OTHER PUBLICATIONS

Beaven, "Marterial Properties and Applications of Pyrolite Carbon", *Materials Engineering*, Feb. 1990.

"Researchers at Bowman Gray Discover that Backflow of Stomach Acid Causes Choking Spells in Adults, May be a Cause of Sudden Infant Death", *PR Newswire*, The Point-Cast Network, Source: Bowman GrayBaptist Hospital Medical Center, Dec. 6, 1996, p. 1.

Rupp, et al., "Endoscopic Antireflux Techniques Endoluminal and Laparoscopic", *Endoscopy*, vol. 4, No. 2, Apr. 1994, pp. 353–369.

Shafik, "Intraesophageal Polytef Injection for the Treatment of Reflux Esophagitis", *Surgical Endoscopy*, vol. 10, No. 3, Mar. 1996, pp. 329–331.

O'Connor et al., "Endoscopic Placement of collagen at the Lower Esophageal Sphincter to Inhibit Gastroesophageal Reflux: A Pilot Study of 10 Medically Intractable Patients", *Gastrointestinal Endoscopy*, vol. 34, No. 2, Mar.–Apr. 1988, pp. 106–112.

Smith et al., "Evaluation of Polydimethylsiloxane as an Alternative in the Endoscopic Treatment of Vesicoureteral Reflux", *J. Urol.*, 152:1221–1224, 1994.

Walker et al., "Injectable Bioglass as a Potential Substitute for Injectable Polytetrafluoroethylene", *J. Urol.*, 148:645–7, 1992.

Malizia, Jr. et al., "Migration and Granulomatous Reaction After Periurethral Injection of Polytef (Teflon)", *JAMA*, 251:3277–3281, 1984.

Stroobants et al., "Pulmonary Migration Following Periurethral Polytetrafluoroethylene Injection for Urinary Incontinence", *J. Urol.*, 142:821–822, 1989.

Politano et al., "Periurethral Teflon Injection for Urinary Incontinence", *U. Urol.*, 111:180–183, 1974.

Boedts et al., "Laryngeal Tissue Responses to Teflon", *Arch. Otolaryng*, 86:110–115, 1967.

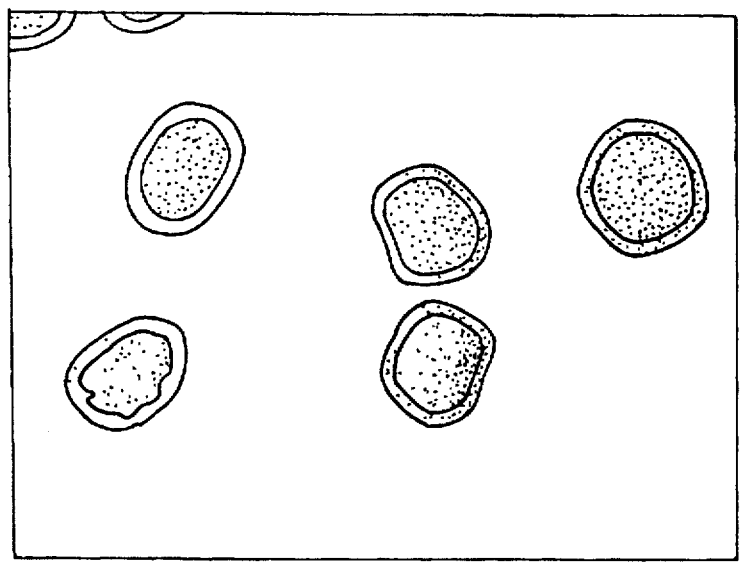

TISSUE INJECTABLE COMPOSITION AND METHOD OF USE

BACKGROUND OF THE INVENTION

This invention relates to an injectable composition of physiologically compatible and appropriately sized particles carried in a lubricative, biologically compatible fluid or gel. The composition is formulated to be delivered into the body to a tissue site through a small-bore instrument to strengthen, bulk-up and otherwise augment the tissue site and surrounding area.

The percutaneous injection of substances into tissues to augment, support, or reconfigure anatomic structure has been the subject of significant research and product development and is well known in the art. See, for example, U.S. Pat. Nos. 4,803,075 and 5,204,382 to Wallace et al., and U.S. Pat. No. 5,258,028 to Ersek et al. Procedures have been described in the medical literature for correction of dermatological, otolaryngological problems and for treatment of urological disorders, e.g., Smith et al., "Evaluation of Polydimethylsiloxane as an Alternative in the Endoscopic Treatment of Vesicoureteral Reflux", *J. Urol.*, 152: 1221–1224, 1994, and Walker et al., "Injectable Bioglass as a Potential Substitute for Injectable Polytetrafluoroethylene", *J. Urol.*, 148:645–7 (1992) and the references cited therein.

Urinary incontinence and vesicourethral reflux are urological disorders that have responded to treatments with augumentive materials. Incontinence occurs when the resistance to urine flow has decreased to the point where the resistance can no longer resist the intra-abdominal pressure. Nearly all procedures developed to restore continence are based on restoring the lost resistance to urine outflow. U.S. Pat. Nos. 5,007,940; 5,158,573; and 5,116,387 to Berg disclose biocompatible compositions comprising discrete, polymeric and silicone rubber bodies injectable into urethral tissue for the purpose of treatment of urinary incontinence by tissue bulking. Further, U.S. Pat. No. 5,451,406 to Lawin, the inventor of the present composition, discloses biocompatible compositions comprising carbon coated substrate particles injectable into a tissue, such as the tissues of and that overlay the urethra and bladder neck, for the purpose of treatment of urinary incontinence by tissue bulking.

The most serious adverse effects that may occur from therapies of this type relate to the migration of the solid materials from the original site of placement into repository sites in various body organs and the chronic inflammatory response of tissue to particles that are too small. These adverse effects are well documented in the urologic literature, specifically in Malizia, A. A., et al., "Migration and Granulomatous Reaction After Periurethral Injection of Polytef (Teflon)", *JAMA* 251:3277–3281 (1984) and Claes, H., Stroobants, D. et al., "Pulmonary Migration Following Periurethral Polytetrafluoroethylene Injection For Urinary Incontinence", *J. Urol.*, 142:821–822 (1989). An important factor in assuring the absence of migration is the administration of properly sized particles. If the particle is too small, it can be engulfed by the body's white cells (phagocytes) and carried to distant organs or be carried away in the microvasculature and travel until it reaches a site of greater constriction. Target organs for deposition include the lungs, liver, spleen, brain, kidney, and lymph nodes.

The use of small diameter particulate spheres, in the range of 1–20 microns, and small elongate fibrils having a diameter in the range 1–20 microns, formed of materials such as cross linked collagen or synthetic polymers suspended in an aqueous medium having biocompatible lubricant has been disclosed in Wallace et al., U.S. Pat. No. 4,803,075. While these materials showed positive, short term augmentation results, this result was short lived as the material had a tendency to migrate and/or be absorbed by the host tissue.

Teflon paste was used early to treat stress urinary incontinence. Politano, V. A., Small, M. P., Harper, J. M., Lynne, C. M., "Periurethral Teflon Injection for Urinary Incontinence", *J.Urol.*, 111:180–183 (1974). The Teflon paste consisted of polytetrafluoroethylene particles in a size range of 1 to 100 microns. More than ninety percent of the particles were in the range of 1 to 40 microns. Malizia, A. A. Reiman, H. M., Myers, R. P., et al., "Migration and Granulomatous Reaction After Periurethral Injection of Polytef (Teflon)", *JAMA,* 251:24:3277–3281 (1984). This product demonstrated foreign body granuloma formation at the injection site and local migration. Boedts, D., Roels, H., Kluyskens, P., "Laryngeal Tissue Responses to Teflon", *Arch Otolaryngol,* 86:562–567 (1967).

In a 1980's study, TEFLON particles were injected periurethrally into monkeys and dogs, approximating the technique used to treat humans. Malizia, A. A. Reiman, H. M., Myers, R. P., et al., "Migration and Granulomatous Reaction After Periurethral Injection of Polytef (Teflon)", *JAMA,* 251:24: 3277–3281 (1984). After 10½ months, local and distant migration, including to the lungs and brains of test animals, was observed. Migration included particles having a greatest dimension of 80 microns. TEFLON granulomas, signifying chronic foreign-body reaction, were found at all injection sites and some sites of distant migration.

Proper particle size selection is important. Studies indicate that a particle size for Teflon (PTFE) in the range of between 1 and 100 microns is unacceptable for injectable material. Particles in this size range show local and distant migration, produce chronic inflammatory response in tissue, and has been associated with clinical complications. Particles that are too large are difficult to deposit e.g. will not go down a needle small enough to have clinical application.

Thus, there remains a need for a treatment that provides a lasting remedy with minimized side effects.

The primary focus of this invention has been directed toward the development of biocompatible, nonmigratory particles that are effectively delivered to the desired tissue site in a lubricative, biocompatible fluid or gel carrier. The preferred carrier shall not cause any deleterious effects at or near the site of particle delivery and will be removed from the site by normal biological or biochemical processes such as excretion or metabolic breakdown.

SUMMARY OF THE INVENTION

In accordance with the present invention there is provided an injectable, biocompatible composition comprised of a plurality of discrete, physiologically compatible, carbon or carbon-coated particles of a predetermined size range and a lubricative fluid or gel in which the particles are carried. The carrier is preferably a biologically compatible solution or suspension. The particles range in size from 100 microns to 1,000 microns in transverse, cross-sectional dimension.

The composition is designed to be delivered into the body through a small-bore needle, cannula, or catheter to a tissue site for the purpose of augmenting the tissue site and surrounding area, thereby correcting a defect, filling a void or strengthening the support structures of the tissue.

The invention is comprised of two components. The first is a plurality of carbon or carbon-coated particles ranging in size as microbeads or microparticles from a minimum of 100 microns to a maximum of 1,000 microns. The carbon-coated particles can be created by subjecting an appropriate, particulate substrate to a coating process in which carbon is deposited as a thin coating or film, thereby creating a particle that has a highly biocompatible surface. The substrate material must be capable of withstanding the high temperature conditions of the coating process. Zirconium oxide and aluminum oxide have been found to be especially suitable as such a substrate. Carbon itself, such as non-pyrolytic carbon, may also be utilized as the particulate substrate. As an alternative to a substrate coated particle, low temperature isotropic (LTI), pyrolytic carbon alone can form a solid pyrolytic carbon bead.

The second component acts as the lubricative carrier for the carbon or carbon-coated particles and in the preferred embodiment is comprised of a suspension, solution, or other biologically compatible fluid or a gel. One example of a biologically compatible carrier is methyl cellulose or other unbranched polysaccharide, either singly or in combination with one or more solutions well known in the art. Other lubricative carriers can include β-glucan, hyaluronic acid and derivatives thereof, polyvinyl pyrrolidone or a hydrogel derivative thereof, dextrans or hydrogel derivatives thereof, glycerol, polyethylene glycol, succinaylated collagen, liquid collagen, and other polysaccharides or biocompatible polymers, either singly or in combination with one or more of the above-referenced solutions. The preferred carrier must be capable of being formulated into a viscous fluid or into a self-supporting gel. For purposes of this invention, the carrier shall be of sufficient viscosity to suspend the particles for sufficient duration to inject the composition.

BRIEF DESCRIPTION OF THE DRAWING

FIG. 1 is a cross-sectional view of coated particles in accordance with the invention.

DETAILED DESCRIPTION OF THE PREFERRED EMBODIMENTS

The invention consists of an injectable composition that is a combination of a plurality of small, smooth-surfaced particles that are carried in a lubricative fluid or gel that is preferably comprised of a biologically compatible, lubricous solution, suspension, other fluid or gel.

In a first embodiment, the particles comprise microbeads or microparticles of a hard, material serving as a substrate and having a thin coating or film of biocompatible, isotropic carbon deposited on their surfaces. The substrate material is preferably radiopaque. Different types of carbon coating processes may be utilized, with the particulate substrate being a substance selected for compatibility with the coating process. As shown in the figure which is a depiction from actual photomicrographs of particles produced in accordance with the present invention, the substrate particles are completely encased by the thin coating. This results in a smooth coated particle with no substrate exposure on the surface of the particle or in contact with tissue when injected.

Low temperature isotropic (LTI) pyrolytic carbon is a preferred carbon coating. Pyrolytic derives from the term pyrolysis, which is a thermal decomposition of hydrocarbons to produce a carbon material. Pyrolytic carbon is produced in a process in which hydrocarbons and alloying gases are decomposed in a fluidized or floating bed. Inert gas flow is used to float the bed and the substrate particles. The hydrocarbon pyrolysis results in high carbon, low hydrogen content spheres, which deposit as solids upon the substrate in the fluidized bed. As they deposit at temperatures of 1200°–1500° C., the spheres may coalesce, deform or grow due to atom movement, resulting in a high density coating. A hard, metallic or ceramic substance capable of withstanding the high temperature conditions of the coating process is the preferred substrate material.

Aluminum oxide is a preferred substrate material. Zirconium oxide has also been found to be especially suitable as such a substrate. However, metallic substrates, including but not limited to medical grade stainless steel, titanium and titanium alloys and all oxide derivatives of each, are also quite acceptable as the substrate material. Using metal particles as substrates has the drawback of high cost. Due to increasing cost pressures, less expensive materials are desirable. Applicants have also found that carbon itself maybe utilized as a satisfactory substrate material which is of low cost for the instant invention. The carbon substrate can be non-pyrolytic carbon. Thus, the beads in one preferred embodiment may be comprised entirely of carbon. In another preferred embodiment, a total pyrolytic carbon particle may comprise the bead.

Ultra-low-temperature isotropic carbon may be applied as a coating in vacuum vapor deposition processes. Carbon can be deposited effectively utilizing ion beams generated from the disassociation of $CO_2$, reactive disassociation in vacuum of a hydrocarbon as a result of a glow discharge, sublimation of a solid graphite source or cathode sputtering of a graphite source, as examples of such processes. Gold has been found to be suitable as a substrate material ideal for vacuum vapor deposited carbon, however, other substrates, including but not limited to nickel, silver, stainless steel, or titanium are also quite acceptable as the substrate material.

Vitreous or glass carbons may also serve as the coating material. These are also isotropic, monolithic carbons, which are formed by pyrolysis of carbonaceous preforms, during which gaseous pyrolysis products diffuse through the shape and are liberated.

The atomic structure of either pyrolitic LTI carbon or vitreous carbon is similar to graphite, the common form of carbon, but the alignment between hexagonal planes of atoms is not as well ordered. Pyrolitic carbon is characterized by a more chaotic atomic structure with warped hexagonal planes, missing atoms and generally a more turbostatic appearance. This results in better bonding between layer planes.

The coating process is applied to small substrate particles to produce final, rounded particles that have a smooth carbon-coated surface in the form of a thin, black film. The resulting smooth surface on the particles enhances their passage through an injection needle, cannula or catheter and into body tissue. The high strength, resistance to breakdown or corrosion, and durability of the carbon coating insures the effective, long term functioning of the particles in tissue augmentation at the injection site. The established biocompatibility of pyrolytic carbon renders it particularly suitable for the anticipated body tissue applications.

After the carbon coating has been applied, the particles are subjected to a cleaning and sieving process to remove contaminants and to separate out particles of a size less than or greater than the desired size range. The particles may range in size from 100 microns to 1,000 microns in average, transverse cross-sectional dimension, and a preferred size range is between 200 and 500 microns. A most preferred size range is between 251 and 300 microns. The most preferred range avoids particle migration from the injection site yet allows injection through a small bore instrument. The substrate particles are initially milled, extruded or otherwise formed to the desired particle size, in a substantially rounded shape prior to being subjected to the coating process. The particles are randomly shaped and rounded, ranging from oblong to generally spherical. The sieving process is such that the minimum particle dimension will pass through a U.S. No. 18 Screen Mesh (1000 micron grid size opening) but will not pass through a U.S. No. 140 Screen Mesh (106 micron grid size). That minimum dimension will be the transverse, cross-sectional dimension on oblong or elongated particles, with that dimension coinciding with the particle diameter on generally spherical particles.

The carrier is preferably an aqueous suspension or solution, other fluid or gel of polymeric chains of B-D-glucose, commonly referred to as β-glucan. The glucose units are linked to each other at the 1-3, 1-4, or 1-6 positions and form polymeric chains ranging to several thousand daltons in weight.

β-Glucan is a naturally occurring constituent of cell walls in essentially all living systems including plants, yeast, bacteria, and mammalian systems. Its effects and modulating actions on living systems have been studied extensively (see Abel, G., and Czop, J. K., "Stimulation of Human Monocyte B-Glucan Receptors by Glucan Particles Induces Production of TNF-∂ and 1L-B", *Int. J. Immunopharmacol.*, 14(8): 1363–1373, 1992 and references included therein). β-glucan, when administered in experimental studies, elicits and augments host defense mechanisms including the steps required to promote healing by first intent, thereby stimulating the reparative processes in the host system. β-glucan is rapidly removed from tissue sites through macrophagic phagocytosis or by enzymatic destruction by serous enzymes. The rapid destruction or removal of β-glucan, as well as its available viscosity and lubricous nature, makes it an optimum carrier for the particles.

Aqueous solutions, suspensions, fluids, or gels of β-glucan can be produced that have favorable physical characteristics as a carrier for solid carbon or carbon-coated particles. The viscosity can vary from a thin liquid to a firm, self-supporting gel. Irrespective of viscosity, the β-glucan has excellent lubricity, thereby creating a particle-carrier composition which is easily administered by delivery to a predetermined body site through a small bore needle, cannula, or catheter. A preferred β-glucan composition is β-D glucan containing 4-0-linked-β-D-glycopyranosyl units and 3-0-linked-β-D-glycopyranosyl units. The carrier will be of sufficient viscosity to assure that the carbon-coated particles remain suspended therein, for sufficient duration to complete the injection procedure.

Another preferred example of an appropriate carrier is methyl cellulose or other linear unbranched polysaccharide. Further examples of appropriate carriers include hyaluronic acid, polyvinyl pyrrolidone or a hydrogel derivative thereof, dextran or a hydrogel derivative thereof, glycerol, polyethylene glycol, succinylated collagen, liquid collagen, oil based emulsions such as corn oil or safflower, or other polysaccharides or biocompatible organic polymers either singly or in combination with one or more of the above-referenced solutions.

In use, the above-described composition will be injected in a fluid state, e.g., as a slurry, fluid suspension or emulsion, or as a gel through a syringe needle or cannula into a body tissue site. When deposited into a soft tissue site, the carrier will disperse or be destroyed as set forth above. The particles are of an optimum size which will prevent their being carried away by capillary blood flow. They will thus remain at the site and will serve to fill voids, provide additional support, or correct other soft-tissue defects.

The composition of the present invention may be utilized in urological applications. The composition may be injected into the tissues of the urinary tract, wherein the injection sites may be, for example, the sub-mucosal tissue plane of the bladder neck and/or urethra, the muscle fiber and adjoining tissues of the urethra and the tissues of the bladder neck. These injection procedures are well described in the urologic literature, as demonstrated in Politano, V. A., "Periurethral Polytetrafluoroethylene Injection For Urinary Incontinence", *J. Urol.*, 127: 439–442 (1982), and Appell, R. A., "Collagen Injection Therapy For Urinary Incontinence", *Urol. Clin. N. Amer.*, 21: 177–182 (1994). The resulting bulking or augmentation of the urethral and bladder neck tissue will reduce the size of the bladder outlet and thus assist in controlling the patient's incontinence.

The present composition is also useful in fecal incontinence applications. U.S. Pat. No. 5,480,644 to Freed discloses the use of collagen formulations and methods of repairing structurally defective or inadequately functioning muscles of the anal sphincter. The compositions may be injected into the tissue of the anal canal, wherein the selected site may be, for example, the internal or external anal sphincter tissue. The resulting bulking or augmentation of the tissue will restrict the size of the sphincter or anal passage and thus assist in overcoming fecal incontinence.

Applicants also believe the present composition can be utilized in gastric reflux applications. The composition may be injected into the tissue of the upper gastrointestinal tract, wherein the selected site may be, for example, the cardiac orifice of the stomach which opens into the esophagus. The resulting bulking or augmentation of the tissue will restrict the size of the passage and thus assist in overcoming gastric fluids refluxing into the esophagus.

Experimental Results

In an experimental study, twelve dogs were implanted with a composition comprised of:

pyrolytic isotropic LTI carbon-coated zirconium oxide particles in a size range from 260 to 500 microns of a total mass of 400 mg suspended in 1 ml of: β-glucan formulated as a 2.8% weight by weight aqueous suspension, as the carrier. The dosage was titrated to the individual animal but did not exceed 3 ml per animal. The method of implantation was by injection into the periurethral tissues using a needle and syringe. A group of control animals were injected with saline.

Each dog was closely observed over the balance of its time in the study, monitoring morbidity, mortality, body weight, food consumption and signs of overt toxicity. Radiographs were taken postoperatively and prior to necropsy. Hematological, biochemical and urinalysis tests were conducted on all animals pre-test and at three month intervals for one year. Animals were euthanized for necropsy at three, six and twelve months and a thorough postmortem examination conducted. Protocol specified tissues were processed histologically and microscopic examination was conducted.

At each interval, the tissues showed only minor changes at the injection site. There were no signs of overt toxicity. No significant differences were noted in the body weights or weekly food consumption for the treated vs. control animals.

At the twelve month interval, the radiologic location of the carbon-coated beads was similar to that observed in the three and six month intervals. Technique problems at the time of injection had permitted particles to travel beyond the periurethral area in the immediate post-operative phase.

A second series of animal (dog) implants was done using the technique that most closely approximates the intended route of administration in humans, periurethral injection via an endoscope. In addition to the above disclosed composition, a group of dogs were injected with the β-glucan carrier gel alone. Dogs were euthanized at seven and twenty-eight days. The above biochemical and histological examinations were performed in this second series of test animals. There were no remarkable findings.

In summary, both series of animal implants, the dogs examined at three, six and twelve months and those examined at seven and twenty-eight days, show a healing process that is a normal foreign body reaction. The surrounding tissue quickly passes from an acute to sub-acute inflammatory phase and by three months, mature collagen has formed around the implanted carbon coated beads which remains stable through the first twelve months. No overt signs of toxicity were observed at any time. No evidence of migration of the implant material was noted.

These studies were conducted in accordance with good laboratory practices. They confirmed the handling characteristics of the test material as favorable; the material was easily injected with minimal to moderate resistance.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. An injectable, biocompatible composition for tissue augmentation comprising:

a plurality of discrete particles in a carrier, wherein each particle includes a substrate particle with a carbon coating over the surface thereof, each of said substrate particles manufactured from a compound selected from the group consisting of aluminum oxide and carbon, and have an average transverse cross sectional dimension of between 100 and 1,000 microns, further, wherein the carrier is a biocompatible medium having sufficient fluidity to carry and deliver the particles, and has lubricative qualities.

2. The composition of claim 1 wherein said carbon coating is isotropic carbon.

3. The composition of claim 1 wherein said carbon coating is pyrolytic, isotropic carbon.

4. The composition of claim 1 wherein said carbon coating is a smooth surface film.

5. The composition of claim 1 wherein said substrate particles are of rounded shape and said dimension is between 200 microns and 500 microns.

6. The composition of claim 1 wherein said substrate particles are of rounded shape and said dimension is between 251 microns and 300 microns.

7. The composition of claim 1 wherein said average transverse cross section dimension is between 251 microns and 300 microns.

8. An injectable, biocompatible composition for tissue augmentation comprising:

a plurality of discrete particles of pyrolytic carbon in a carrier, and having an average transverse cross sectional dimension of between 100 and 1,000 microns and the carrier is a biocompatible medium having sufficient fluidity to carry and deliver the particles, and has lubricative qualities.

9. An injectable, biocompatible composition for tissue augmentation comprising:

a plurality of discrete particles in a carrier, wherein each of the particles includes a substrate particle with a carbon coating over the surface thereof and have an average transverse cross sectional dimension of between 100 and 1,000 microns and the carrier is a biocompatible medium having sufficient fluidity to carry and deliver the particles, wherein said carrier is a solution, suspension, or gel of polysaccharides.

10. The composition of claim 9 wherein said polysaccharides are linear, unbranched polysaccharides.

11. The composition of claim 9 wherein said carrier is a solution, suspension, or gel of methyl cellulose.

12. The method of claim 9 wherein said carrier is β-glucan.

13. A method for augmenting tissue in a human patient comprising injecting into a tissue site in the patient a composition comprising a plurality of discrete, carbon or carbon-coated particles having an average, transverse, cross-sectional dimension of between 100 and 1,000 microns in a biocompatible carrier having sufficient fluidity to carry and deliver the particles and has lubricative qualities, wherein the tissue site is the coronary orifice to the stomach.

14. The method of claim 13 wherein said carrier is β-glucan.

15. A method for augmenting tissue in a human patient comprising injecting into a tissue site in the patient a composition comprising a plurality of discrete, carbon or carbon-coated particles having an average, transverse, cross-sectional dimension of between 100 and 1,000 microns in a biocompatible carrier having sufficient fluidity to carry and deliver the particles and has lubricative qualities, wherein the tissue site is the anal canal.

16. The method of claim 15 wherein the tissue site is the internal sphincter muscle of the anal canal.

17. The method of claim 15 wherein the tissue site is the external sphincter muscle of the anal canal.

18. The method of claim 15 wherein said substrate particles are of rounded shape and said dimension is between 200 microns and 500 microns.

19. The method of claim 15 wherein said substrate particles are of rounded shape and said dimension is between 251 microns and 300 microns.

* * * * *